United States Patent [19]

Hedrich

[11] 4,154,599
[45] May 15, 1979

[54] ALKYLTHIOAMINOACRYLONITRILES AND USE AS HERBICIDES

[75] Inventor: Loren W. Hedrich, Overland Park, Kans.

[73] Assignee: Gulf Oil Corporation, Pittsburgh, Pa.

[21] Appl. No.: 838,523

[22] Filed: Oct. 3, 1977

[51] Int. Cl.$^2$ ............................................... A01N 9/12
[52] U.S. Cl. ................................... 71/98; 260/465 E
[58] Field of Search .................................. 71/98, 105

[56] References Cited

U.S. PATENT DOCUMENTS

| 3,723,498 | 3/1973 | Joos ............................................. 71/98 |
| 3,865,863 | 2/1975 | Field et al. ................................. 71/105 |

FOREIGN PATENT DOCUMENTS 4521120  3/1963  Japan.

Primary Examiner—Catherine L. Mills
Attorney, Agent, or Firm—Carl A. Cline

[57] ABSTRACT

New compounds which are useful as herbicides have the general structural formula

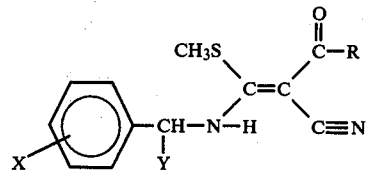

in which R is methoxy, amino, dimethylamino or straight chain $C_1$ to $C_3$ monoalkylamino, X is H, nitro, methoxy, methyl, Cl or F and Y is H or methyl.

8 Claims, No Drawings

ALKYLTHIOAMINOACRYLONITRILES AND USE AS HERBICIDES

DESCRIPTION OF THE INVENTION

(a) Background

In U.S. Pat. No. 3,865,863 there is disclosed a class of herbicidal compounds having the general structural formula:

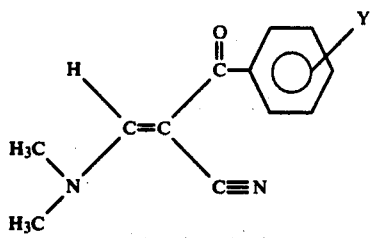

However, many acyl and carbamyl derivatives of acrylonitrile are completely non-phytotoxic or possess no practical utility for this purpose. By way of illustration, the compounds having the following structural formulas have no substantial utility as herbicides:

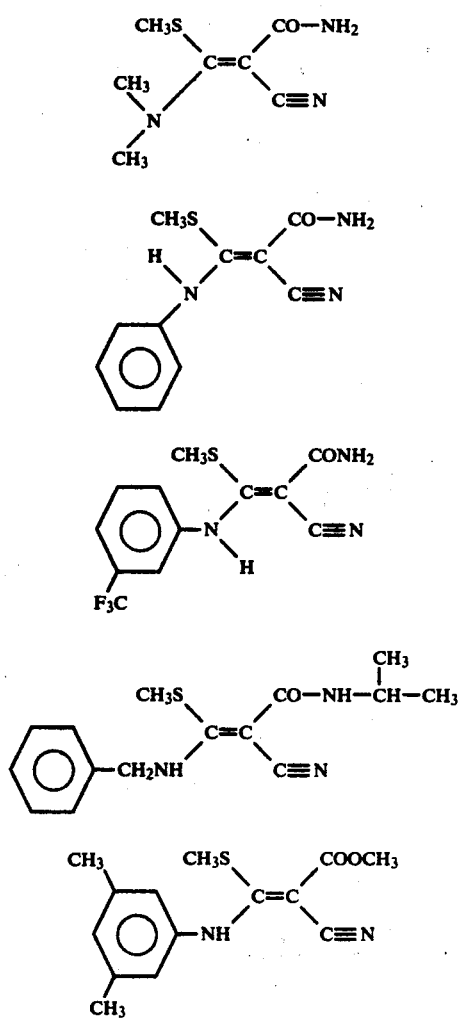

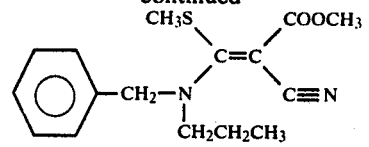

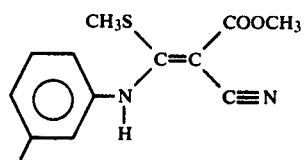

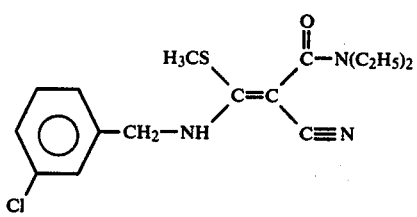

(b) Summary of the Invention

Although many compounds of closely related structural formulas are substantially non-phytotoxic, I have discovered a class of compounds which are effective as selective herbicides at low to moderate application rates, both pre- and post-emergently. These compounds have the general structural formula

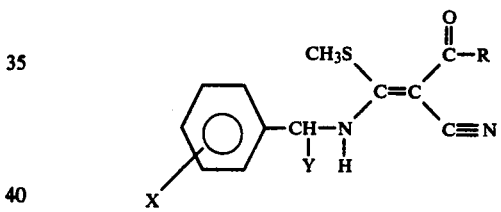

in which R is methoxy, amino, dimethylamino or straight chain $C_1$ to $C_3$ monoalkylamino, X is hydrogen, nitro, methoxy, methyl, chloro or fluoro, located in either or both meta and para positions and Y is hydrogen or methyl. In general, the compounds are preferred in which R is methoxy or amino. Alkyl substituents on the amide nitrogen do not generally enhance herbicidal activity and two larger alkyl substituents in this position are likely to render the compound non-phytotoxic. The substituent X may be in either or both meta and para position on the benzyl ring. Ortho substituents, however have an adverse effect on phytotoxic properties. The compound having the following structural formula, for example, has no substantial utility as a herbicide.

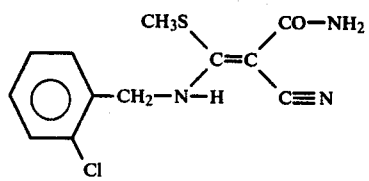

Although the selectivity patterns vary from compound to compound, in general the novel selective herbicides of this invention are most useful for post-emergent control of broadleaf weeds in such crops as oats, peanuts, corn, rice and wheat.

Preparation of the Herbicides

Starting materials were prepared according to Gompper and Toepfl, *Chem. Ber.*, 95, 2861 (1962). These include 2-cyano-3,3-bismethylthioacrylamide and methyl 2-cyano-3,3-bismethylthioacrylate having the structural formulas,

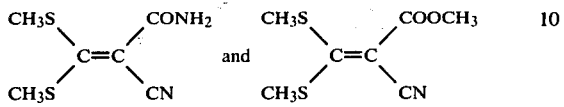

prepared from the corresponding cyanoacetyl compounds. The substituted benzylamine starting materials were purchased or made by means of the Leuckart Wallach reaction, Organic Reactions, vol. 5, page 301 (1949).

General procedures for the preparation of substituted cyanoacetamides and for the final products are illustrated below:

(a) Preparation of Substituted 2-cyanoacetamides

A mixture of 25 mmol of the desired amine and 25 mmol of methyl cyanoacetate in 50 ml of methanol was refluxed overnight. On cooling the solids crystallized and were removed by filtration. In the case of liquid products the solvent was distilled under reduced pressure.

(b) Preparation of 2,3,3-trisubstituted acrylonitriles

A mixture of the 2-cyano-3,3-bisalkylthioacrylamide or acrylate and an equimolar portion of the desired amine (20–25 mmol of each) in 50 ml ethanol was refluxed overnight. A 10% NaOH solution was used to trap the methyl mercaptan evolved. Solids crystallized on cooling. Liquid products, usually oils which decomposed on attempted distillation, were isolated by distilling the solvent. Yields ranged from 70–95%.

Compounds made by the illustrated procedures include those in the following table.

Compounds of the Formula

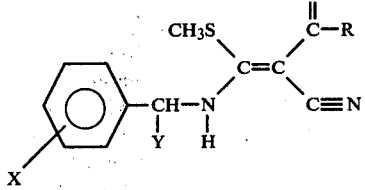

| No. | X | Y | R | m.p. or b.p. (° C.) |
|---|---|---|---|---|
| 1 | H | H | —NH₂ | 112°–15° |
| 2 | p-chloro | H | —NH₂ | 115°–17° |
| 3 | p-fluoro | H | —NH₂ | 132° |
| 4 | 3,4-dichloro | H | —NH₂ | 141°–43° |
| 5 | m-chloro | H | —NH₂ | 110°–15° |
| 6 | H | —CH₃ | —NH₂ | 166°–67° |
| 7 | p-fluoro | —CH₃ | —NH₂ | 95°–96° |
| 8 | m-chloro | H | —NHCH₂CH₂CH₃ | oil |
| 9 | p-methoxy | H | —NH₂ | 118°–20° |
| 10 | m-nitro | H | —NH₂ | 126°–30° |
| 11 | H | H | —OCH₃ | oil |
| 12 | p-chloro | H | —OCH₃ | 93°–94° |
| 13 | p-methoxy | H | —OCH₃ | 64°–66° |
| 14 | p-fluoro | H | —OCH₃ | oil |
| 15 | 3,4-dichloro | H | —OCH₃ | 119°–20° |
| 16 | m-chloro | H | —OCH₃ | 85°–87° |
| 17 | H | —CH₃ | —OCH₃ | oil |
| 18 | p-fluoro | —CH₃ | —OCH₃ | oil |
| 19 | p-fluoro | —CH₃ | —NHC₂H₅ | oil |

Compounds of the Formula

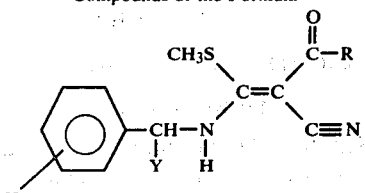

| No. | X | Y | R | m.p. or b.p. (° C.) |
|---|---|---|---|---|
| 20 | H | —CH₃ | —NHC₂H₅ | oil |
| 21 | H | —CH₃ | —N(CH₃)₂ | oil |
| 22 | p-fluoro | —CH₃ | —N(CH₃)₂ | oil |
| 23 | p-fluoro | —CH₃ | —NHCH₃ | 127°–130° |
| 24 | p-chloro | —CH₃ | —NH₂ | 133°–135° |
| 25 | p-chloro | —CH₃ | —OCH₃ | oil |

Combating Unwanted Vegetation

The novel herbicides may be used selectively to combat unwanted vegetation, both post- and pre-emergently at application rates of 5 lb. per acre or less. Higher application rates may be used pre-emergently if a prolonged effect is desired. However, the high activity of the compounds makes it necessary to apply the compounds in combination with an inert carrier or diluent, preferably water. So as to obtain a uniform dispersion in water, a surface active agent is also required. The dispersible concentrated formulations may be either in the form of liquid solutions or dispersions, or wettable powders. For pre-emergent use, the herbicides may also be applied in the form of dry granules, which may be made from solutions of the compounds and inert solids, such as clay, according to customary practice. There are described below illustrative procedures for herbicidal use of the compounds under controlled conditions in the greenhouse so as to obtain data on phytotoxic activity and selectivity.

(1) Post-Emergent Use

An aqueous dispersion of each active compound was prepared by combining 0.4 gram of the compound with about 4 ml of a solvent-emulsifier mixture (3 parts of a commercial polyoxyethylated vegetable oil emulsifier, one part xylene, one part kerosene) and then adding water, with stirring, to a final volume of 40 ml.

The 24 species of plants on which each compound was tested were planted in disposable plastic pots in a greenhouse. Ten to eighteen days after emergence of the plants, three pots of each species were sprayed at each rate with an aqueous dispersion of the active compound prepared as described above, at rates of both 1 lb. and 3 lb. of active compound per acre and at a spray volume of 60 gallons per acre. Approximately one week after the spray application the plants were observed and results were rated according to the following schedule:

DEGREE OF EFFECT

0 = no effect
1 = slight effect
2 = moderate effect
3 = severe effect
4 = maximum effect (all plants died)

The same rating schedule was employed to judge pre-emergent results obtained according to the procedure below.

(2) Pre-Emergent Use

A solution of each active compound was prepared by dissolving 290 mg of the compound to be tested in 200 ml of acetone. Disposable paper trays about 2½ inches deep were filled with soil and sprayed with the acetone solution at rates of 3 lb. and 1 lb. of active chemical per acre of sprayed area, were seeded with 24 species of plant seeds and were then covered with about ¼ inch of soil. Twenty-one days after seeding and treatment the plantings were examined and herbicidal effect was rated according to the above schedule.

Results are tabulated below.

Results of Pre- and Postemergent Use of Herbicides

| Species | Appl'n. Rate (lb/A) | 1 Pre | 1 Post | 2 Pre | 2 Post | 3 Pre | 3 Post | 4 Pre | 4 Post | 5 Pre | 5 Post | 6 Pre | 6 Post |
|---|---|---|---|---|---|---|---|---|---|---|---|---|---|
| Cocklebur | 3 | 0 | 4 | 0 | 4 | 2 | 4 | | 4 | 0 | 4 | 1 | 3 |
| (*Xanthium pensylvanicum*) | 1 | 0 | 2 | 0 | 4 | 0 | 4 | | 4 | | 2 | 0 | 1 |
| Lambsquarters | 3 | 4 | 4 | 4 | 4 | 4 | 4 | 4 | 4 | 4 | 4 | 4 | 4 |
| (*Chenopodium album*) | 1 | 4 | 4 | 4 | 4 | 4 | 4 | | 1 | | 3 | 4 | 4 |
| Morning glory | 3 | 0 | 1 | 0 | 3 | 2 | 4 | | 3 | 0 | 4 | 3 | 2 |
| (*Ipomea purpurea*) | 1 | 0 | 0 | 0 | 2 | 0 | 3 | | 2 | | 2 | 0 | 1 |
| Pigweed | 3 | 3 | 2 | 4 | 4 | 4 | 4 | | 4 | 2 | 2 | 4 | 4 |
| (*Amaranthus retroflexus*) | 1 | 2 | 3 | 4 | 4 | 4 | 1 | | 0 | | 0 | 1 | 2 |
| Wild buckwheat | 3 | 3 | 4 | 4 | 4 | 4 | 4 | | 4 | 4 | 4 | 3 | 4 |
| (*Polygonum convolvulus*) | 1 | 2 | 4 | 2 | 4 | 2 | 4 | | 3 | | 3 | 1 | 4 |
| Wild mustard | 3 | 3 | 4 | 4 | 4 | 4 | 4 | | 4 | 4 | 4 | 4 | 4 |
| (*Brassica kaber*) | 1 | 3 | 4 | 4 | 4 | 3 | 4 | | 4 | | 4 | 4 | 4 |
| Barnyard grass | 3 | 0 | 2 | 0 | 2 | 3 | 3 | | 1 | 0 | 1 | 3 | 1 |
| (*Echinochloa crusgalli*) | 1 | 0 | 1 | 0 | 2 | 0 | 1 | | 0 | | 0 | 2 | 0 |
| Crabgrass | 3 | 1 | 0 | 2 | 0 | 2 | 4 | | 1 | 0 | 0 | 4 | 1 |
| (*Digitaria sanguinalis*) | 1 | 0 | 0 | 0 | 0 | 0 | 0 | | 0 | | 0 | 1 | 0 |
| Downey brome | 3 | 0 | 0 | 1 | 1 | 2 | 1 | | 1 | 0 | 0 | 1 | 0 |
| (*Bromus tectorum*) | 1 | 0 | 0 | 0 | 0 | 0 | 0 | | 0 | | 0 | 0 | 0 |
| Giant foxtail | 3 | 1 | 0 | 0 | 2 | 1 | 3 | | 2 | 0 | 0 | 3 | 1 |
| (*Setaria faberii*) | 1 | 0 | 0 | 0 | 0 | 0 | 0 | | 0 | | 0 | 1 | 0 |
| Green foxtail | 3 | 0 | 1 | 1 | 3 | 4 | 4 | | 3 | 0 | 4 | 3 | 3 |
| (*Setaria viridis*) | 1 | 0 | 0 | 0 | 2 | 1 | 4 | | 1 | | 1 | 2 | 2 |
| Nutsedge | 3 | 0 | 0 | 0 | 0 | 0 | 0 | | 0 | 0 | 0 | 0 | 0 |
| (*Cyperus esculentus*) | 1 | 0 | 0 | 0 | 0 | 0 | 0 | | 0 | | 0 | 0 | 0 |
| Shattercane | 3 | 0 | 0 | 0 | 2 | 0 | 4 | | 0 | 0 | 1 | 1 | 0 |
| (*Sorghum bicolor*) | 1 | 0 | 0 | 0 | 1 | 0 | 0 | | 0 | | 0 | 1 | 0 |
| Wild oats | 3 | 0 | 0 | 0 | 3 | 0 | 1 | | 0 | 0 | 1 | 0 | 0 |
| (*Avena fatua*) | 1 | 0 | 0 | 0 | 1 | 0 | 0 | | 0 | | 0 | 0 | 0 |
| Alfalfa | 3 | 3 | 1 | 1 | 2 | 3 | 3 | | 3 | 2 | 1 | 1 | 4 |
| (*Medicago sativa*) | 1 | 0 | 0 | 0 | 1 | 2 | 3 | | 2 | | 1 | 3 | 2 |
| Cotton | 3 | 1 | 0 | 0 | 4 | 0 | 4 | | 4 | 0 | 3 | 0 | 3 |
| (*Gossypium herbaceum*) | 1 | 0 | 0 | 0 | 4 | 0 | 2 | | 3 | | 1 | 0 | 1 |
| Peanuts | 3 | 0 | 0 | 0 | 1 | 0 | 1 | | 1 | 0 | 0 | 0 | 1 |
| *Arachis hypogaea* | 1 | 0 | 0 | 0 | 0 | 0 | 0 | | 0 | | 0 | | 0 |
| Soybeans | 3 | 1 | 2 | 0 | 4 | 2 | 3 | | 4 | 0 | 3 | 3 | 4 |
| (*Soja max*) | 1 | 0 | 1 | 0 | 3 | 0 | 0 | | 3 | | 2 | 0 | 1 |
| Sugar beets | 3 | 3 | 4 | 4 | 4 | 4 | 4 | | 4 | 1 | 4 | 2 | 3 |
| (*Beta vulgaris*) | 1 | 1 | 4 | 2 | 4 | 2 | 2 | | 1 | | 1 | 0 | 1 |
| Tomato | 3 | 1 | 1 | 1 | 4 | 4 | 4 | | 4 | 0 | 3 | 4 | 3 |
| (*Lycopersicum esculentum*) | 1 | 1 | 1 | 0 | 4 | 0 | 4 | | 3 | | 1 | 0 | 3 |
| Corn | 3 | 0 | 0 | 0 | 1 | 0 | 3 | | 0 | 0 | 0 | 1 | 0 |
| (*Zea mays*) | 1 | 0 | 0 | 0 | 0 | 0 | 0 | | 0 | | 0 | 0 | 0 |
| Grain sorghum | 3 | 0 | 0 | 0 | 2 | 0 | 4 | | 0 | 0 | 0 | 1 | 0 |
| (*Sorghum vulgare*) | 1 | 0 | 0 | 0 | 1 | 0 | 0 | | 0 | | 0 | 0 | 0 |
| Rice | 3 | 0 | 1 | 0 | 2 | 0 | 2 | — | 0 | 0 | 0 | 1 | 0 |
| (*Oryza satyia*) | 1 | 0 | 1 | 0 | 0 | 0 | 0 | — | 0 | 0 | 0 | 0 | 0 |
| Wheat | 3 | 0 | 1 | 0 | 3 | 2 | 2 | — | 1 | 0 | 1 | 1 | 1 |
| (*Tricutucum aestivum*) | 1 | 0 | 1 | 0 | 1 | 1 | 0 | — | 0 | 0 | 0 | 0 | 0 |

| Species | Appl'n. Rate (lb/A) | 7 Pre | 7 Post | 8 Pre | 8 Post | 9 Pre | 9 Post | 10 Pre | 10 Post | 11 Pre | 11 Post | 12 Pre | 12 Post |
|---|---|---|---|---|---|---|---|---|---|---|---|---|---|
| Cocklebur | 3 | 1 | 4 | 0 | 4 | 0 | 4 | 0 | 3 | 0 | 4 | 0 | 4 |
| (*Xanthium pensylvanicum*) | 1 | 0 | 4 | | 4 | | 0 | | 2 | 0 | 0 | 0 | 3 |
| Lambsquarters | 3 | 4 | 4 | 4 | 4 | 3 | 4 | 4 | 4 | 4 | 4 | 4 | 4 |
| (*Chenopodium album*) | 1 | 4 | 4 | | 4 | | 3 | | 2 | 3 | 2 | | 4 |
| Morning glory | 3 | 1 | 4 | 0 | 4 | 0 | 2 | 0 | 1 | 0 | 2 | 0 | 3 |
| (*Ipomea purpurea*) | 1 | 0 | 3 | | 4 | | 0 | | 0 | 0 | 1 | 0 | 0 |
| Pigweed | 3 | 4 | 4 | 4 | 4 | 3 | 4 | 4 | 3 | 2 | 2 | 1 | 3 |
| (*Amaranthus retroflexus*) | 1 | 4 | 4 | | 4 | | 1 | | 1 | 1 | 0 | 1 | 3 |
| Wild buckwheat | 3 | 4 | 4 | 0 | 4 | 0 | 2 | 2 | | 1 | 4 | 2 | 4 |
| (*Polygonom convolvulus*) | 1 | 3 | 4 | | 4 | | 2 | | 2 | 1 | 1 | 2 | 4 |
| Wild mustard | 3 | 4 | 4 | 3 | 4 | 0 | 1 | 1 | 4 | 4 | 4 | 3 | 4 |
| (*Brassica kaber*) | 1 | 4 | 4 | | 4 | | 0 | | 1 | 4 | 0 | 2 | 4 |
| Barnyard grass | 3 | 3 | 4 | 1 | 4 | 0 | 1 | 0 | 0 | 0 | 4 | 0 | 3 |
| (*Echinochloa crusgalli*) | 1 | 1 | 1 | | 3 | | 0 | | 0 | 0 | 0 | 0 | 1 |

-continued

Results of Pre- and Postemergent Use of Herbicides

| Species | | | | | | | | | | | | | | |
|---|---|---|---|---|---|---|---|---|---|---|---|---|---|---|
| Crabgrass | 3 | 4 | 2 | 1 | 4 | 0 | 0 | 0 | 0 | 0 | 3 | 1 | 2 |
| (*Digitaria sanguinalis*) | 1 | 4 | 1 | | 4 | | 0 | | 0 | 0 | 0 | 0 | 0 |
| Downey brome | 3 | 2 | 2 | 0 | 2 | 0 | 1 | 0 | 1 | 0 | 2 | 2 | 3 |
| (*Bromus tectorum*) | 1 | 0 | 1 | | 1 | | 0 | | 0 | 0 | 0 | 0 | 1 |
| Giant foxtail | 3 | 3 | 4 | 0 | 4 | 0 | 1 | 0 | 1 | 0 | 3 | 0 | 2 |
| (*Setaria faberil*) | 1 | 3 | 2 | | 4 | | 0 | | 0 | 0 | 1 | 0 | 0 |
| Green foxtail | 3 | 4 | 4 | 3 | 4 | 0 | 1 | 0 | 1 | 0 | 4 | 0 | 4 |
| (*Setaria viridis*) | 1 | 1 | 2 | | 4 | | 0 | | 0 | 0 | 0 | 0 | 1 |
| Nutsedge | 3 | 0 | 0 | 0 | 0 | 0 | 0 | 0 | 0 | 0 | 0 | 0 | 0 |
| (*Cyperos esculentus*) | 1 | 0 | 0 | | 0 | | 0 | | 0 | 0 | 0 | 0 | 0 |
| Shattercane | 3 | 1 | 3 | 0 | 4 | 0 | 0 | 0 | 0 | 0 | 2 | 0 | 3 |
| (*Sorghom bicolor*) | 1 | 0 | 1 | | 4 | | 0 | | 0 | 0 | 0 | 0 | 0 |
| Wild oats | 3 | 2 | 3 | 0 | 1 | 0 | 0 | 0 | 1 | 0 | 4 | 1 | 3 |
| (*Avena fatua*) | 1 | 0 | 1 | | 1 | | 0 | | 0 | 0 | 1 | 0 | 2 |
| Alfalfa | 3 | 2 | 3 | 4 | 4 | 0 | | 0 | 1 | 1 | 3 | 4 | 4 |
| (*Medicago sativa*) | 1 | 0 | 1 | | 4 | | | | 0 | 0 | 1 | 0 | 1 |
| Cotton | 3 | 3 | 4 | 0 | 4 | 0 | 0 | 0 | 1 | 0 | 3 | 1 | 4 |
| (*Gossypium herbaceum*) | 1 | 0 | 3 | | 3 | | 0 | | 0 | 0 | 1 | 0 | 3 |
| Peanuts | 3 | 0 | 1 | 0 | 3 | 0 | 0 | 0 | 0 | 0 | 0 | 0 | 1 |
| (*Arachis hypogaea*) | 1 | 0 | 1 | | 3 | | 0 | | 0 | 0 | 0 | 0 | 1 |
| Soybeans | 3 | 2 | 4 | 0 | 4 | 0 | 1 | 0 | 1 | 0 | 2 | 0 | 3 |
| *Soja max*) | 1 | 0 | 2 | | 4 | | 1 | | 0 | 0 | 1 | 0 | 2 |
| Sugar beets | 3 | 4 | 4 | 0 | 4 | 0 | 2 | 0 | 2 | 4 | 4 | 3 | 4 |
| (*Beta vulgaris*) | 1 | 4 | 4 | | 4 | | 1 | | 0 | 4 | 1 | 2 | 4 |
| Tomato | 3 | 4 | 4 | 1 | 4 | 0 | 1 | 0 | 2 | 2 | 3 | 1 | 4 |
| (*Lycopersicum esculentum*) | 1 | 3 | 4 | | 4 | | 0 | | 0 | 0 | 2 | 0 | 4 |
| Corn | 3 | 1 | 1 | 0 | 4 | 0 | 0 | 0 | 1 | 0 | 1 | 0 | 1 |
| (*Zea mays*) | 1 | 0 | 0 | | 3 | | 0 | | 0 | 0 | 0 | 0 | 0 |
| Grain sorghum | 3 | 1 | 2 | 0 | 4 | 0 | 0 | 0 | 0 | 0 | 1 | 0 | 2 |
| (*Sorghum vulgare*) | 1 | 0 | 0 | | 4 | | 0 | | 0 | 0 | 0 | 0 | 0 |
| Rice | 3 | 2 | 2 | 0 | 4 | 0 | 0 | 0 | 0 | 0 | 3 | 0 | 3 |
| (*Oryza sativa*) | 1 | 0 | 1 | 0 | 3 | | 0 | | 0 | 0 | 0 | 0 | 1 |
| Wheat | 3 | 1 | 3 | 0 | 1 | 0 | 0 | 0 | 1 | 0 | 4 | 0 | 4 |
| (*Triticum aestivum*) | 1 | 0 | 1 | 0 | 0 | | 0 | | 0 | 0 | 1 | 0 | 2 |

| | | Compound No. | | | | | | | | | | | |
|---|---|---|---|---|---|---|---|---|---|---|---|---|---|
| | Appl'n. | 13 | | 14 | | 15 | | 16 | | 17 | | 18 | |
| | Rate | Mode of Application | | | | | | | | | | | |
| Species | (lb/A) | Pre | Post | Pre | Post | Pre | Post | Pre | Post | Pre | Post | Pre | Post |
| Cocklebur | 3 | | 4 | 0 | 4 | | 4 | 0 | 4 | 0 | 3 | 0 | 4 |
| (*Xanthium pensylvanicum*) | 1 | | 4 | 0 | 4 | | 4 | 0 | 4 | 0 | 2 | 0 | 4 |
| Lambsquarters | 3 | | 4 | 4 | 4 | | 4 | 4 | 4 | 4 | 4 | 4 | 4 |
| (*Chenopodium album*) | 1 | | 3 | 4 | 4 | | 4 | | 4 | 1 | 4 | 4 | 4 |
| Morning glory | 3 | | 4 | 0 | 4 | | 4 | 0 | 3 | 0 | 4 | 0 | 4 |
| *Ipomea purpurea*) | 1 | | 2 | 0 | 3 | | 4 | 0 | 1 | 0 | 2 | 0 | 3 |
| Pigweed | 3 | | 4 | 2 | 3 | | 4 | 3 | 2 | 1 | 4 | 2 | 4 |
| (*Amaranthus retroflexus*) | 1 | | 1 | 1 | 0 | | 1 | 0 | 0 | 0 | 0 | 2 | 0 |
| Wild buckwheat | 3 | | 4 | 4 | 4 | | 4 | 4 | 4 | 2 | 4 | 4 | 4 |
| (*Polygonum convolvulus*) | 1 | | 4 | 3 | 4 | | 4 | 4 | 4 | 1 | 4 | 4 | 4 |
| Wild mustard | 3 | | 4 | 4 | 4 | | 4 | 4 | 4 | 4 | 4 | 4 | 4 |
| (*Brassica kaber*) | 1 | | 4 | 3 | 4 | | 4 | 4 | 4 | 3 | 4 | 4 | 4 |
| Barnyard grass | 3 | | 0 | 0 | 4 | | 1 | 0 | 3 | 1 | 4 | 3 | 4 |
| (*Ehinochica crusgalli*) | 1 | | 0 | 0 | 1 | | 0 | 0 | 2 | 0 | 3 | 2 | 2 |
| Crabgrass | 3 | | 3 | 4 | 4 | | 2 | 2 | 2 | 3 | 4 | 4 | 3 |
| (*Digitaria sanguinalis*) | 1 | | 0 | 2 | 1 | | 0 | 1 | 0 | 0 | 1 | 3 | 2 |
| Downey brome | 3 | | 2 | 3 | 2 | | 1 | 3 | 4 | 1 | 3 | 3 | 3 |
| (*Bromus tectorum*) | 1 | | 0 | 1 | 0 | | 0 | 1 | 1 | 0 | 1 | 2 | 2 |
| Gaint foxtail | 3 | | 2 | 1 | 4 | | 2 | 1 | 3 | 4 | 4 | 3 | 4 |
| (*Setaria faberil*) | 1 | | 0 | 1 | 1 | | 0 | 0 | 0 | 0 | 4 | 2 | 3 |
| Green foxtail | 3 | | 3 | 2 | 4 | | 3 | 1 | 4 | 4 | 4 | 4 | 4 |
| (*Setaria virdis*) | 1 | | 2 | 1 | 4 | | 3 | 0 | 3 | 0 | 4 | 4 | 4 |
| Nutsedge | 3 | | 0 | 0 | 0 | | 0 | 0 | 0 | 0 | 0 | 0 | 0 |
| (*Cyperus esclentus*) | 1 | | 0 | 0 | 0 | | 0 | 0 | 0 | 0 | 0 | 0 | 0 |
| Shattercane | 3 | | 3 | 0 | 3 | | 2 | 0 | 2 | 0 | 4 | 0 | 4 |
| (*Sorghum bicolor*) | 1 | | 1 | 0 | 1 | | 1 | 0 | 0 | 0 | 1 | 0 | 2 |
| Wild oats | 3 | | 3 | 0 | 4 | | 3 | 1 | 4 | 0 | 4 | 1 | 4 |
| (*Avena fatua*) | 1 | | 0 | 0 | 1 | | 2 | 0 | 2 | 0 | 1 | 1 | 3 |
| Alfalfa | 3 | | 4 | 4 | 4 | | 4 | 4 | 4 | 3 | 4 | 4 | 4 |
| (*Medicago sativa*) | 1 | | 3 | 3 | 4 | | 3 | 1 | 1 | 2 | 3 | 4 | 4 |
| Cotton | 3 | | 4 | 0 | 4 | | 4 | 0 | 4 | 0 | 3 | 0 | 4 |
| (*Gossypium herbaceum*) | 1 | | 3 | 0 | 4 | | 4 | 0 | 3 | 0 | 1 | 0 | 4 |
| Peanuts | 3 | | 1 | 0 | 1 | | 1 | 0 | 2 | 0 | 2 | 0 | 2 |
| (*Arachis hypogaea*) | 1 | | 0 | 0 | 0 | | 1 | 0 | 1 | 0 | 0 | 0 | 1 |
| Soybeans | 3 | | 2 | 0 | 3 | | 4 | 0 | 4 | 1 | 3 | 0 | 4 |
| (*Soja max*) | 1 | | 2 | 0 | 4 | | 4 | 0 | 2 | 0 | 2 | 0 | 3 |
| Sugar beets | 3 | | 4 | 0 | 4 | | 4 | 2 | 4 | 2 | 4 | 4 | 4 |
| (*Beta vulgaris*) | 1 | | 4 | 0 | 4 | | 4 | 1 | 3 | 1 | 4 | 4 | 4 |
| Tomato | 3 | | 4 | 2 | 4 | | 4 | 1 | 4 | 1 | 4 | 3 | 4 |
| (*Lycopersicum esculentum*) | 1 | | 4 | 1 | 4 | | 3 | 0 | 4 | 0 | 4 | 3 | 4 |

-continued

| Results of Pre- and Postemergent Use of Herbicides | | | | | | | | | | | | | |
|---|---|---|---|---|---|---|---|---|---|---|---|---|---|
| Corn | 3 | | 0 | 0 | 1 | | 2 | 0 | 1 | 0 | 2 | 0 | 2 |
| (Zea mays) | 1 | | 0 | 0 | 0 | | 0 | 0 | 0 | 0 | 1 | 0 | 0 |
| Grain sorghum | 3 | | 2 | 0 | 3 | | 1 | 0 | 2 | 0 | 2 | 0 | 4 |
| (Sorghum vulgare) | 1 | 0 | 0 | 1 | | 0 | 0 | 0 | 0 | 0 | 0 | 2 | |
| Rice | 3 | 0 | 2 | 1 | 3 | 0 | 2 | 2 | 3 | 0 | 2 | 1 | 4 |
| (Oryza sativa) | 1 | 0 | 1 | 0 | 2 | 0 | 1 | 0 | 1 | 0 | 1 | 0 | 2 |
| Wheat | 3 | 0 | 4 | 1 | 4 | 0 | 4 | 0 | 4 | 0 | 3 | 1 | |
| (Triticum aestivum) | 1 | 0 | 1 | 0 | 2 | 0 | 2 | 0 | 2 | 0 | 1 | 1 | 3 |

I claim:

1. A selective agricultural herbicide composition comprising a herbicidally effective amount of a compound having the structural formula

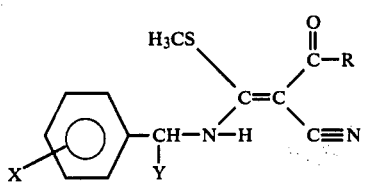

in which R is methoxy, amino, dimethylamino or straight chain $C_1$ to $C_3$ monoalkylamino, X is hydrogen, nitro, methoxy, methyl, chloro or fluoro located in either or both meta and para positions and Y is hydrogen or methyl, said compound being combined with a surface active agent and an inert carrier.

2. A composition according to claim 1 which contains a herbicidally effective amount of 3-(p-chlorobenzylamino)-2-cyano-3-methylthioacrylamide.

3. A composition according to claim 1 which contains a herbicidally effective amount of 2-cyano-3-(p-fluorobenzylamino)-3-methylthioacrylamide.

4. A composition according to claim 1 which contains a herbicidally effective amount of 3-(m-chlorobenzylamino)-2-cyano-3-methylthio-N-propylacrylamide.

5. A composition according to claim 1 which contains a herbicidally effective amount of methyl 2-cyano-3-(p-fluorobenzylamino)-3-methylthioacrylate.

6. A composition according to claim 1 which contains a herbicidally effective amount of methyl 2-cyano-3-(3,4-dichlorobenzylamino)-3-methylthioacrylate.

7. A composition according to claim 1 which contains a herbicidally effective amount of methyl 2-cyano-3-[1-(p-fluorophenyl)-ethylamino]-3-methylthioacrylate.

8. The method of combating unwanted vegetation either pre- or post-emergently comprising applying a herbicidally effective amount of a compound having the structural formula

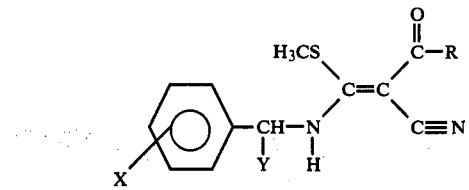

in which R is methoxy, amino, dimethylamino or straight chain $C_1$ to $C_3$ monoalkylamino, X is hydrogen nitro, methoxy, methyl, chloro or fluoro located in either or both meta and para positions and Y is hydrogen or methyl.

* * * * *

UNITED STATES PATENT AND TRADEMARK OFFICE
CERTIFICATE OF CORRECTION

PATENT NO. : 4,154,599  Page 1 of 2

DATED : May 15, 1979

INVENTOR(S) : Loren W. Hedrich

It is certified that error appears in the above-identified patent and that said Letters Patent are hereby corrected as shown below:

Column 3, line 53, under heading m.p. or b.p.(°C.), which reads "112-15°", should read -- 112°-14° --.

Column 5-6, Table entitled Results of Pre-& Postemergent Use of Herbicides, Compound 6, Species - (Arachis hypogaea), should have a -- 0 -- under Pre.

In the same Table, compounds 1 thru 6, under Species "(Oryza satyia)" should be spelled -- Oryza sativa --; "(Tricutucum aestivum)" should be spelled -- Triticum aestivum --; compounds 7 thru 12, "(Polygonom convolvulus)" should be spelled --(Polygonum convolvulus)--; "(Setaria faberil)" should be spelled -- Setaria faberii --; "(Cyperos esculentus)" should be spelled -- Cyperus esculentus --; "(Sorghom bicolor)" should be spelled -- Sorghum bicolor --; compounds 13 thru 18, "(Ehinochica crusgalli)" should be spelled -- Echinochloa crusgalli --; "(Setaria faberil)" should be spelled -- Setaria faberii --; "(Cyperus esclentus)" should be spelled -- Cyperus esculentus --.

Column 9 and 10, Specie (Sorghum vulgare), results should read

| 13 | | 14 | | 15 | | 16 | | 17 | | 18 | |
|---|---|---|---|---|---|---|---|---|---|---|---|
| Pre | Post | Pre | Post | Pre | Post | Pre | Post | Pre | Post | Pre | Post |
| 0 | 0 | | 1 | | 0 | 0 | 0 | 0 | 0 | 0 | 2 |

UNITED STATES PATENT AND TRADEMARK OFFICE
CERTIFICATE OF CORRECTION

PATENT NO. : 4,154,599

DATED : May 15, 1979

INVENTOR(S) : Loren W. Hedrich

It is certified that error appears in the above-identified patent and that said Letters Patent are hereby corrected as shown below:

Column 9 and 10, Compound 18, Specie wheat, results under Post should be -- 4 --.

Signed and Sealed this

Twenty-third Day of October 1979

[SEAL]

Attest:

RUTH C. MASON
*Attesting Officer*

LUTRELLE F. PARKER
*Acting Commissioner of Patents and Trademarks*